United States Patent [19]

Sanger et al.

[11] Patent Number: 4,725,603
[45] Date of Patent: Feb. 16, 1988

[54] NOVEL TREATMENT

[75] Inventors: Gareth J. Sanger, Sawbridgeworth; Wesley D. Miner, Harlow, both of England

[73] Assignee: Beecham Group, p.l.c., Brentford, England

[21] Appl. No.: 876,724

[22] Filed: Jun. 20, 1986

[30] Foreign Application Priority Data

Jun. 22, 1985 [GB] United Kingdom ............... 8515845

[51] Int. Cl.⁴ ........................................... A61K 31/44
[52] U.S. Cl. ................................................... 514/305
[58] Field of Search ............................. 514/282, 305

[56] References Cited

U.S. PATENT DOCUMENTS 4,612,319 9/1986 King ................................... 514/505

Primary Examiner—Stanley J. Friedman
Attorney, Agent, or Firm—James F. Haley, Jr.; Teresa L. Solomon

[57] ABSTRACT

A method of treatment of migraine, cluster headaches and trigeminal neuralgia, radiation or cytotoxic agent induced nausea and vomiting and/or cardiac arrhythmia in mammals, including humans, which method comprises administering an effective amount of a compound of formula (I) or a pharmaceutically acceptable salt thereof:

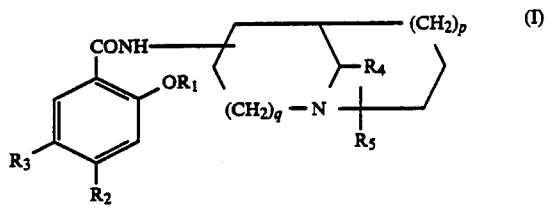

wherein:

$R_1$ is $C_{1-6}$ alkyl;

$R_2$ is amino or $C_{1-7}$ acylamino;

$R_3$ is halo;

one of $R_4$ and $R_5$ is hydrogen, $C_{1-6}$ alkyl, phenyl or phenyl $C_{1-3}$ alkyl, which phenyl moieties may be substituted by one or more substituents selected from $C_{1-6}$ alkyl, $C_{1-6}$ alkoxy, $CF_3$ or halogen;

the other of $R_4$ and $R_5$ is hydrogen or $C_{1-6}$ alkyl;

p is 0 to 2; and q is 0 to 3.

7 Claims, No Drawings

NOVEL TREATMENT

This invention relates to a method of treatment of migraine, cluster headaches and trigeminal neuralgia, radiation or cytotoxic agent induced nausea and vomiting and/or cardiac arrhythmia in mammals, including humans, and to the use of compounds in the preparation of a medicament for the treatment of such conditions.

EP No. 94742 discloses a class of substituted azabicyclo compounds which are described as having dopamine antagonist activity, useful in the treatment of disorders relating to impaired gastro-intestinal motility, such as retarded gastric emptying, dyspepsia, flatulence, oesphageal reflux and peptic ulcer. Depending on their balance between peripheral and central action on the nervous system, they may also be used in the treatment of emesis and/or the treatment of disorders of the central nervous system, such as psychosis.

It has now been discovered that certain of these compounds are 5-HT receptor antagonists and are therefore useful in the treatment of migraine, cluster headaches and trigeminal neuralgia. They also block the emetic response induced by radiation and cytotoxic agents such as cisplatin, doxorubicin and cyclophosphamide, and are therefore of use in the treatment of nausea and vomiting associated with cancer therapy. In addition, they have been found to have anti-arrhythmic activity.

Accordingly, the present invention provides a method of treatment of migraine, cluster headaches and trigeminal neuralgia, radiation or cytotoxic agent induced nausea and vomiting and/or cardiac arrhythmia in mammals, including humans, which method comprises administering an effective amount of a compound of formula (I) or a pharmaceutically acceptable salt thereof:

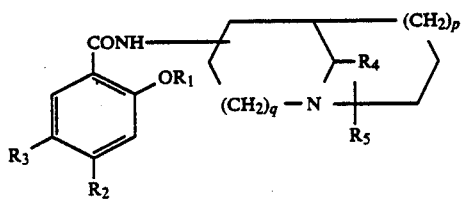

wherein:
$R_1$ is $C_{1-6}$ alkyl;
$R_2$ is amino or $C_{1-7}$ acylamino;
$R_3$ is halo;
one of $R_4$ and $R_5$ is hydrogen, $C_{1-6}$ alkyl, phenyl or phenyl $C_{1-3}$ alkyl, which phenyl moieties may be substituted by one or more substituents selected from $C_{1-6}$ alkyl, $C_{1-6}$ alkoxy, $CF_3$ or halogen;
the other of $R_4$ and $R_5$ is hydrogen or $C_{1-6}$ alkyl;
p is 0 to 2; and
q is 0 to 3.

Examples of $R_1$ include methyl, ethyl, n- and iso-propyl. Preferably $R_1$ is methyl.

Examples of $R_2$ include amino and $C_{1-6}$ alkanoylamino, such as formylamino, acetylamino, propionylamino, n-and iso-butyrylamino. Often $R_2$ is amino or acetylamino, preferably amino.

Examples of $R_3$ include chloro, bromo and fluoro. Preferably $R_3$ is chloro or bromo, most preferably chloro.

Examples of $R_4$ and $R_5$ include hydrogen, methyl, ethyl, n- and iso-propyl, n-, iso-, sec- and tert-butyl, and phenyl, benzyl or phenethyl wherein any phenyl moiety is optionally substituted by one or two of chloro, bromo, fluoro, $CF_3$, methoxy, ethoxy, n- or iso-propoxy, methyl, ethyl, n- and iso-propyl. Preferably $R_4$ is hydrogen and $R_5$ is hydrogen.

P may be 0, 1 or 2, preferably 1.

q may be 0, 1, 2 or 3, favourably 1 or 2, preferably 1.

Often p and q will both be 1 or 2, preferably they will both be 1.

Preferably the nitrogen atom in the azabicyclic side chain is separated from the amide nitrogen by at least two carbon atoms.

The pharmaceutically acceptable salts of the compounds of the formula (I) include acid addition salts with conventional acids such as hydrochloric, hydrobromic, boric, phosphoric, sulphuric acids and pharmaceutically acceptable organic acids such as acetic, tartaric, maleic, citric, succinic, benzoic, ascorbic, methanesulphonic, α-keto glutaric, α-glycerophosphoric, and glucose-1-phosphoric acids.

The pharmaceutically acceptable salts of the compounds of the formula (I) are usually acid addition salts with acids such as hydrochloric, hydrobromic, phosphoric, sulphuric, citric, tartaric, lactic and acetic acid. Preferably the acid addition salt is the hydrochloride salt.

Pharmaceutically acceptable salts also include quaternary derivatives, examples of which include the compounds quaternised by compounds such as $R_{10}$-Z wherein $R_{10}$ is $C_{1-6}$ alkyl, phenyl-$C_{1-6}$ alkyl or $C_{5-7}$ cycloalkyl, and Z is a radical corresponding to an anion of an acid. Suitable examples of $R_{10}$ include methyl, ethyl and n- and iso-propyl; and benzyl and phenethyl. Suitable examples of Z include halide such as chloride, bromide and iodide.

Pharmaceutically acceptable salts also include internal salts such as pharmaceutically acceptable N-oxides.

The compounds of the formula (I), and their pharmaceutically acceptable salts may also form pharmaceutically acceptable solvates, such as hydrates which are included whereever a compound of formula (I) or a salt thereof is herein referred to.

It will of course be realised that some of the compounds of the formula (I) have chiral or prochiral centres, and thus are capable of existing in a number of stereoisomeric forms, including enantiomers. The invention extends to each of these stereoisomeric forms (including enantiomers), and to mixtures thereof (including racemates). The different stereoisomeric forms may be separated one from the other by the usual methods.

Compounds of the formula (I) may be prepared in accordance with the methods described in EP No. 94742 or by analogous methods thereto.

The administration of the compound of formula (I) or a pharmaceutically acceptable salt thereof may be by way of oral or parenteral administration.

An amount effective to treat the disorders hereinbefore described depends on the relative efficacies of the compounds of the invention, the nature and severity of the disorder being treated and the weight of the mammal. However, a unit dose for a 70 kg adult will normally contain 0.1 to 100 mg for example 0.2 to 5mg, of the compound of formula (I) or a pharmaceutically acceptable salt thereof. Unit doses may be administered once or more than once a day, for example, 2, 3 or 4 times a day, more usually 1 to 3 times a day, that is in the range of approximately 0.0002 to 5 mg/kg/day, more usually 0.0004 to 2.5 mg/kg/day.

No adverse toxicological effects are indicated at any of the aforementioned dosage ranges.

It is preferred that the compound of formula (I) or a pharmaceutically acceptable salt thereof is administered in the form of a unit dose pharmaceutical composition in which is combined with a pharmaceutically acceptable carrier.

Such compositions are prepared by admixture and are suitably adapted for oral or parenteral administration, and as such may be in the form of tablets, capsules, oral liquid preparations, powders, granules, lozenges, reconstitutable powders, injectable and infusable solutions or suspensions or suppositories. Orally administrable compositions are preferred, since they are more convenient for general use.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art, for example with an enteric coating.

Suitable fillers for use include cellulose, mannitol, lactose and other similar agents. Suitable disintegrants include starch, polyvinylpolypyrrolidone and starch derivatives such as sodium starch glycollate. Suitable lubricants include, for example, magnesium stearate.

Suitable pharmaceutically acceptable wetting agents include sodium lauryl sulphate. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

Oral liquid preparations are usually in the form of aqueous or oily suspensions, solutions, emulsions, syrups, or elixirs or are presented as a dry product for reconstitution with water or other suitable vehicle before use. Such liquid preparations may contain conventional additives such as suspending agents, emulsifying agents, non-aqueous vehicles (which may include edible oils), preservatives, and flavouring or colouring agents The oral compositions may be prepared by conventional methods of blending, filling or tabletting. Repeated blending operations may be used to distribute the active agent throughout those compositions employing large quantities of fillers. Such operations are, of course, conventional in the art.

For parenteral administration, fluid unit dose forms are prepared containing a compound of the present invention and a sterile vehicle. The compound, depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure of ethylene oxide before suspending in the sterile vehicle. Advantageously, a surfactant or wetting agent is included in the composition to facilitate uniform distribution of the compound.

The present invention also provides the use of a compound of formula (I) or a pharmaceutically acceptable salt thereof in the preparation of a medicament for use in the treatment of migraine, cluster headaches and trigeminal neuralgia, radiation or cytotoxic agent induced nausea and vomiting and/or cardiac arrhythmia in mammals, including humans. Such treatment may be carried out in the manner as hereinbefore described.

The present invention further provides a pharmaceutical composition for use in the treatment of migraine, cluster headaches and trigeminal neuralgia, radiation or cytotoxic agent induced nausea and vomiting and/or cardiac arrhythmia which comprises an effective amount of a compound of formula (I) or a pharmaceutically acceptable salt thereof and a pharmaceutically acceptable carrier. Such compositions may be prepared in the manner as hereinbefore described.

The following pharmacological data illustrate the invention.

Compound No. 6 (Example 9) (from EP No. 94742) is ($\pm$)4-amino-5-chloro-2-methoxy-N-(4[1-azabicyclo[3,3,1]-nonyl])-benzamide.

Pharmacological Data

1. Antagonism of the von Bezold-Jarisch reflex

The compounds were evaluated for antagonism of the von Bezold-Jarisch reflex evoked by 5HT in the anaesthetised rat according to the following method.

Male rats 250–350 g, were anaesthetised with urethane (1.25 g/kg intraperitoneally) and blood pressure and heart rate recorded as described by Fozard J. R. et al., J. Cardiovasc. Pharmacol. 2, 229–245 (1980). A submaximal dose of 5-HT (6–20 $\mu$g/kg) was given repeatedly by the intravenous route and changes in heart rate quantified. Test Compounds were given intravenously and the concentration required to reduce the 5HT-evoked response to 50% of the control response ($ED_{50}$) was then determined.

The result obtained with the compound of Example 9 is shown below:

| Compound No. | $ED_{50}$ mg/kg i.v. |
|---|---|
| 6 [Example 9] | 0.0033 |

2. Inhibition of Chemotherapy Induced Nausea and Vomiting

Adult male ferrets (initial body weight 1.3–1.8 kg) were individually housed, fed once daily (200 g Chum Puppy Food plus 50 g Lab Diet A) and were supplied with water ad libitum. Additionally, each animal was given ¼ pint of milk daily during an acclimatization period.

To facilitate intravenous administration of drugs, a chronic indwelling catheter was surgically implanted into the jugular vein using a modification of the technique described by Florczyk and Schurig, 1981 (Pharmacol. Biochem. Behav., 14, 255–257). Prior to surgery each animal was sedated with ketamine hydrochloride (40 mg/animal intramuscularly) and anaesthetised with a halothane-$N_2O$-$O_2$ mixture. A four day recovery period was allowed before commencement of an experiment.

For each group of animals, a preliminary study was carried out to establish an intravenous dose level of cisplatin which would give a consistent and reproducible emetic response. The appropriate dose of test compound was administered intravenously twice to each animal; 30 minutes before and 45 minutes after dosing with cisplatin. Running controls received vehicle and cisplatin only.

A single emetic response commenced when an animal assumed a characteric posture with retching and was concluded when either vomitus was expelled or was present in the mouth as evidenced by a chewing movement. The total number of emetic responses was determined during the five hour period following administration of cisplatin and the number of animals completely protected from emesis determined for each treatment.

All solutions were prepared in water for injection B. P. Cisplatin was prepared from vials of Neoplatin for injection (Mead Johnson; dose volume of 2.1 mg/kg).

The result obtained with the compound of Example 9 is shown below:

| Treatment Dose mg/kg i.v. Administered twice | Dose of Cisplatin mg/kg i.v. | No. of animals completely protected/No. of animals used |
| --- | --- | --- |
| Vehicle 6 [Example 9] | 10 | 0/10 |
| 0.65 | 10 | 1/6 |
| 1.25 | 10 | 4/6 |
| 2.5 | 10 | 3/6 |

3. Inhibition of Radiation Induced Nausea and Vomiting.

Ferrets with surgically implanted indwelling venous cannulae were restrained in a purposely constructed perspex box, and exposed to ionising radiation from an X-ray source. The X-ray source (Machlett, Model OEG-50, Tungsten Anode) was approximately 25 cm from the upper surface of the animal, and was operated at 50 Kv and 20 mA through a 1 mm beryllium window and 0.18 mm aluminium filtration. The whole body of each animal was irradiated for 10.4 minutes at a dose rate of 300 rad/minute. At the completion of irradiation animals were put back in their pens and observed for at least 120 minutes. The time from the start of irradiation to the first emetic episode (latency period), and the number of emetic episodes were recorded. Latency period was taken as 120 minutes in animals completely protected from vomiting. The test compound was injected intravenously 2 to 4 minutes before the start of irradiation.

The result obtained with the compound of example 9 is shown below:

| Treatment Dose mg/kg i.v. | No. of animals completely protected/N- of animals used | Group Mean ($\pm$s.e.m.) | |
| --- | --- | --- | --- |
| | | Latency period | No. of emetic episodes |
| Vehicle 6 [Example 9] | 0/5 | 19.4 ($\pm$1.1) | 28.8 ($\pm$1.3) |
| 0.25 | 1/4 | 64.0 ($\pm$18.7)* | 7.8 ($\pm$3.3)* |
| 1.25 | 2/5 | 79.2 ($\pm$16.7)** | 1.2 ($\pm$0.6)** |

Compared with controls
*$P < 0.05$,
**$P < 0.01$ Man-Whitney 'U' test.

4. Antiarrhythmic Activity

The compound of Example 9 was tested for antiarrhythmic activity in the dog coronary ligation model (method: Harris, A., Circulation Res. 1, 1318–1328, 1950).

Results (max. effects)

1. dog: no effect on day 1-arrhythmias (=arrhythmias 24 h after coronary ligation) at 0.5–3.0 mg/kg; ectopic beats on day 2 (=arrhythmias 48 h after coronary ligation) were reduced by 41% and 76% at 2.0 and 3.0 mg/kg, respectively.

2 dog: ectopic beats on day 1 were reduced by 63, 69 and 82% at 1,0, 2,0 and 3,0 mg/kg, respectively. Arrhythmias on day 2 were antagonized by 89 and 100% at 0.5 and 1.0 mg/kg, respectively.

Other compounds of the Examples described in EP No. 94742 within formula (I) may be tested and found to be active in tests 1, 2, 3 and 4.

We claim:

1. A method of treatment of radiation or cytotoxic agent induced nausea and vomiting in mammals, including humans, which method comprises administering to a mammal in need of such treatment an effective amount of a compound of formula I or a pharmaceutically acceptable salt thereof:

wherein:
$R_1$ is $C_{1-6}$ alkyl;
$R_2$ is amino or $C_{1-7}$ acylamino;
$R_3$ is halo;
$R_4$ and $R_5$ are both hydrogen;
p is 0 or 1; and
q is 1.

2. A method according to claim 1 wherein $R_1$ is methyl.

3. A method according to claim 1 wherein $R_2$ is amino or acetylamino.

4. A method according to claim 1 wherein $R_3$ is chloro or bromo.

5. A method according to claim 1 wherein p is 1 and q is 1.

6. A method according to claim 1 wherein the compound of formula (I) is ($\pm$)-4-amino-5-chloro-2-methoxy-N-(4[1-azabicyclo[3,3,1]-nonyl])-benzamide or a pharmaceutically acceptable salt thereof.

7. A method according to claim 1 wherein the method is for the treatment of radiation or cytotoxic agent induced nausea and vomiting.